(12) United States Patent
Spears et al.

(10) Patent No.: US 7,399,620 B2
(45) Date of Patent: Jul. 15, 2008

(54) POLYPEPTIDES AND BACTERIAL STRAINS FOR INCREASED PROTEIN PRODUCTION

(75) Inventors: Melissa Spears, St. Louis, MO (US); Greg Davis, Webster Groves, MO (US); Henry George, Belleville, IL (US)

(73) Assignee: Sigma-Aldrich Co., St. Louis, MO (US)

( * ) Notice: Subject to any disclaimer, the term of this patent is extended or adjusted under 35 U.S.C. 154(b) by 0 days.

(21) Appl. No.: 11/376,284

(22) Filed: Mar. 15, 2006

(65) Prior Publication Data

US 2007/0218538 A1 Sep. 20, 2007

(51) Int. Cl.
*C12N 9/00* (2006.01)
*C12N 15/00* (2006.01)
*C12N 9/20* (2006.01)
*C12Q 1/68* (2006.01)

(52) U.S. Cl. .................. 435/183; 435/252.3; 435/320.1; 435/6; 435/252.33

(58) Field of Classification Search .................. 435/183, 435/252.3, 320.1, 6, 252.33; 536/23.2
See application file for complete search history.

(56) References Cited

U.S. PATENT DOCUMENTS

| | | | |
|---|---|---|---|
| 5,698,421 A | 12/1997 | Lambowitz et al. | |
| 5,804,418 A | 9/1998 | Lambowitz et al. | |
| 5,869,634 A | 2/1999 | Lambowitz et al. | |
| 6,001,608 A | 12/1999 | Lambowitz et al. | |
| 6,027,895 A | 2/2000 | Lambowitz et al. | |
| 6,306,596 B1 | 10/2001 | Lambowitz et al. | |
| 6,610,836 B1 * | 8/2003 | Breton et al. | 536/23.1 |
| 6,632,639 B1 | 10/2003 | Dreyfus et al. | |
| 2002/0034559 A1 | 3/2002 | Ambuel et al. | |
| 2004/0029231 A1 | 2/2004 | Freyfus et al. | |
| 2004/0126842 A1 | 7/2004 | Dreyfus et al. | |

OTHER PUBLICATIONS

Altschul, S.F., et al., "Basic Local Alignment Search Tool", *J Mol Bio* (1990) pp. 403-410, vol. 215.
Altschul, S.F., et al., "Gapped Blast and PSI-Blast: a new generation of protein database search programs", *Nucleic Acids Res* (1997) pp. 3389-3402, vol. 25, No. 17.
Babitzke, P., et al., The Ams (altered mRNA stability) protein and ribonuclease E are encoded by the same structural gene of *Escherichia coli*, *PNAS* (1991) pp. 1-5, vol. 88.
Brosius, J., et al., "Gene Organization and Primary Structure of a ribosomal RNA Operon from *Escherichia coli*", *J Mol Biol* (1981) pp. 107-127, vol. 148.
Casaregola, S., et al., "Cloning and Analysis of the Entire *Escherichia coli ams* Gene *ams* is Identical to *hmp1* and Encodes a 114kDa Protein that Migrates as a 180kDa Protein", *J Mol Bio* (1992) pp. 30-40, vol. 228.
Claverie-Martin, F., et al., "Cloning of the altered mRNA Stability (*ams*) Gene of *Escherichia coli* K-12", *J Bacteriol* (1989), pp. 5479-5486, vol. 171, No. 10.

Coburn, G.A., et al., "Degradation of mRNA in *Escherichia coli*: An Old Problem with Some New Twists", *Prog Nucleic Acid Res Mol Biol* (1999) pp. 55-108, vol. 62.
Cohen, S.N., et al., "RNase E: still a wonderfully mysterious enzyme", *Mol Micro* (1997) pp. 1099-1106, vol. 23(6).
Colbere-Garapin, F., et al., "A New Dominant Hybrid Selective Marker for Higher Eukaryotic Cells", *J Mol Biol* (1981) pp. 1-14, vol. 150.
Condon, C., et al., "Identification of the gene encoding the 5S ribosomal RNA maturase in *Bacillus subtilis*: Mature 5S rRNA is dispensable for ribosome function", *RNA* (2001) pp. 242-253, vol. 7.
Cormack, R.S., et al., "Structural Requirements for the Processing of *Escherichia coli* 5 S Riobosomal RNA by RNase E in vitro", *J Mol Bio* (1992) pp. 1078-1090, vol. 228, No. 4.
Ehretsmann, C.P., et al., "mRNA degradation in procaryotes", *FASEB J* (1992) pp. 3186-3192, vol. 6.
Engelhard, E.K., et al., "The insect tracheal system: A conduit for the systemic spread of *Autographa californica* M nuclear polyhedrosis virus", *PNAS USA Microb* (1994) pp. 3224-3227.
Grunberg-Mango, M., "Messenge RNA Stability and Its Role in Control of Gene Expression in Bacteria and Phages", *Annu Rev Genet* (1999) pp. 193-227, vol. 33.
Harrington, J.L., et al., "Formation of *de novo* centromeres and construction of first-generation human artificial microchromosomes", *Nat Genet* (1997) pp. 345-355, vol. 15.
Hartman, S.C., et al., "Two dominant-acting selectable markers for gene transfer studies in mammalian cells", *Proc Nat'l Acad Sci USA Cell Bio* (1988) pp. 8047-8051, vol. 85.
Jermutus, L., et al., "Recent advances in producing and selecting functional proteins by using cell-fee translation", *Cur Opin Biotechnol* (1998) pp. 534-548, vol. 9(5).
Karlin, S., et al. "Applications and statistics for multiple high-scoring segments in molecular sequences", *PNAS USA Evolution* (1993) pp. 5873-5877, vol. 90.
Kido, M., et al., "RNase E Polypeptides Lacking a Carboxyl-Terminal Half Suppress a *mukB* Mutation in *Escherichia coli*", *J Bacteriol* (1996) pp. 3917-3925, vol. 178, No. 13.
Kushner, S.R., "mRNA Decay in *Escherichia coli* Comes of Age", *J Bacteriol* (2002) pp. 4658-4665, vol. 184, No. 17.
Lin-Chao, S., et al., "Effects of Nucleotide Sequence on the Specificity if *rne*-dependent and RNase E-mediated Cleavages of RNA 1 Encoded by the pBR322 Plasmid", *J Biol Chem* (1994) pp. 10797-10803, vol. 269, No. 14.
Logan, J. et al., "Adenovirus tripartite leader sequence enhances translation of mRNAs late after infection", *PNAS USA Biochem* (1984) pp. 3655-3659, vol. 81.
Lopez, P.J., et al., "The C-terminal half of RNase E, which organizes the *Escherichia coli* degradosome, participates in mRNA degradation but not rRNA processing in vivo", *Mol Micro* (1999) pp. 188-199, vol. 33, No. 1.
Lowy, I. et al., "Isolation of Transforming DNA: Cloning the Hamster aprt Gene", *Cell* (1980) pp. 817-823, vol. 22.

(Continued)

Primary Examiner—Maryam Monshipouri
(74) *Attorney, Agent, or Firm*—Polsinelli Shalton Flanigan Suelthaus PC

(57) ABSTRACT

The invention provides polypeptides, nucleic acid sequences, bacterial strains, methods and kits for producing exogenous protein. More specifically, the invention provides RNase E polypeptides that posses impaired mRNA degrading activity and efficient rRNA and tRNA processing activity. These polypeptides may be utilized for producing exogenous protein.

23 Claims, 5 Drawing Sheets

OTHER PUBLICATIONS

Makarova, O.V., et al., "Transcribing of *Escherichia coli* genes with mutant T7 RNA polymerases: Stability of *lacZ* mRNA inversely correlates with polymerase speed", *PNAS USA Microbio* (1995) pp. 12250-12254, vol. 92.

Makrides, S.C., "Strategies for Achieving High-Level Expression of genes in *Escherichia Coli*",*Microbio Reviews* (1996) pp. 512-538, vol. 60, No. 3.

Ow, M.C., et al., "Initiation of tRNA maturation by RNase E is essential for cell viability in *E. coli*", *Genes and Dev* (2002) pp. 1102-1115, vol. 16.

Regnier, P., et al., "Degradation of mRNA in bacteria: emergence of ubiquitous features", *BioEssays* (2000) pp. 235-244, vol. 22.

Rhodes, C.A., et al., "Transformation of Maize by Electroporation of Embryos", *Meth Mol Biol* (1995) pp. 121-131, vol. 55.

Saldanha, R., et al., "RNA and Protein Catalysis in Group II Intron Splicing and Mobility Reactions Using Purified Components", *Biochem* (1999) pp. 9069-9083, vol. 38.

Sandig, V., et al., "Gene Transfer into Hepatocytes and Human Liver Tissue by Baculovirus Vectors", *Hum Gen Ther* (1996) pp. 1937-1945, vol. 7.

Takamatsu, N., et al., "Expression of bacterial chloramphenicol acetyltransferase gene in tobacco plants mediated by TMV-RNA", *EMBO J* (1987) pp. 307-311, vol. 6, No. 2.

Van Heeke, G., et al., "Expression of Human Asparagine Synthetase in *Escherichia coli*", *J Biol Chem* (1989) pp. 5503-5509, vol. 264, No. 10.

Wang, M., et al., "*ard-1*: A human gene that reverses the effects of temperature-sensitive and deletion mutations in the *Escherichia coli rne* gene and encodes an activity producing RNase E-like cleavages", *PNAS Biochem* (1994) pp. 10591-10595, vol. 91.

Wigler, M. et al., "Transfer of Purifed Herpes Virus Thymidine Kinase Gene to Cultured Mouse Cells", *Cell* (1977) pp. 223-232, vol. 11.

Wigler, M., et al., "Transformation of mammalian cells with an amplifiable dominant-acting gene", *PNAS USA Genetics* (1980) pp. 3567-3570, vol. 77, No. 6.

* cited by examiner

POLYPEPTIDES AND BACTERIAL STRAINS FOR INCREASED PROTEIN PRODUCTION

FIELD OF THE INVENTION

The invention relates to the production of exogenous protein. More specifically, the invention relates to polypeptides, nucleic acid sequences, bacterial strains, methods and kits for producing exogenous protein.

BACKGROUND OF THE INVENTION

RNase E is a 5'-end-dependent single strand endoribonuclease (Cormack and Mackie, 1992; Ehretsmann et al., 1992; Lin-Chao et al., 1994) that plays a general role in RNA metabolism and is a principal endoribonuclease in messenger RNA decay (Coburn and Mackie, 1999; Grunberg-Manago, 1999; Regnier and Arraiano, 2000). RNase E is a large, 1061 residue protein (Casaregola et al., 1992). Proteins related to RNase E are found throughout the eubacterial kingdom and in some plants (Condon et al., 2001). The plant homologues are presumably in the chloroplast, which is an organelle of eubacterial origin.

RNase E is believed to be responsible for degrading mRNA and processing rRNA and tRNA (Ow and Kushner, Genes and Development (2002)16:1102-1115). The mRNA degrading activity of RNase E significantly affects the efficiency of E. coli based protein expression systems. Bacteriophage T7 RNA polymerase (RNAP) elongates single strand RNA significantly faster than the E. coli enzyme. When mRNA is transcribed by T7 RNAP, long stretches of ribosome-free message occur. These untranslated mRNAs are very unstable, and their instability correlates with the rate of elongation of T7 PNAP (Makarova et al., Proc. Natl. Acad. Sci. USA 1995, 92, 12250-12254. RNase E is responsible for this rapid functional inactivation.

Furthermore, RNase E is responsible for processing the 9S precursors of the 5S rRNA and for processing tRNA. If the tRNA processing abilities of RNase E are disrupted, decreases in cell growth are observed and may be linked to the fact that RNase E cleavage is the rate-limiting step in the maturation of tRNAs.

The literature describes truncations of RNase E that possess limited ability to degrade mRNA, but maintain, at least in part, the ability to process rRNA and tRNA. The most extreme of these truncations, however, were created on plasmids. RNase E truncations created on plasmids, although relatively simple to construct, have disadvantages including the need to work in a recombination deficient background and the concern that the dose of the complementing gene could vary due to changes in plasmid copy number. Due to these limitations, RNase E mutations on plasmids are not suitable for use in exogenous protein production systems. A need, therefore, exists for a bacterial strain having a chromosomally integrated RNase E mutant that may be utilized to facilitate high levels of exogenous protein production.

SUMMARY OF THE INVENTION

Among the several aspects of the invention, therefore, is a bacterial strain comprising a chromosomally mutated nucleotide sequence that encodes an RNase E polypeptide of the invention in place of the wild-type RNase E. The RNase E polypeptide of the invention possesses impaired ability to degrade mRNA.

Another aspect of the invention is a method of using the bacterial strain of the invention to produce exogenous protein.

Because the RNase E polypeptide of the invention has impaired mRNA degrading abilities, but still supports cell viability, the bacterial strain of the invention has increased protein translation of an exogenous protein compared to a bacterial strain comprising wild-type RNase E.

An additional aspect of the invention is a kit for producing exogenous protein. The kit comprises the bacterial strain of the invention and instructions for using the strain to produce exogenous protein.

Other aspects and features of the invention will be in part apparent and in part pointed out hereinafter.

DETAILED DESCRIPTION

Figure 1:
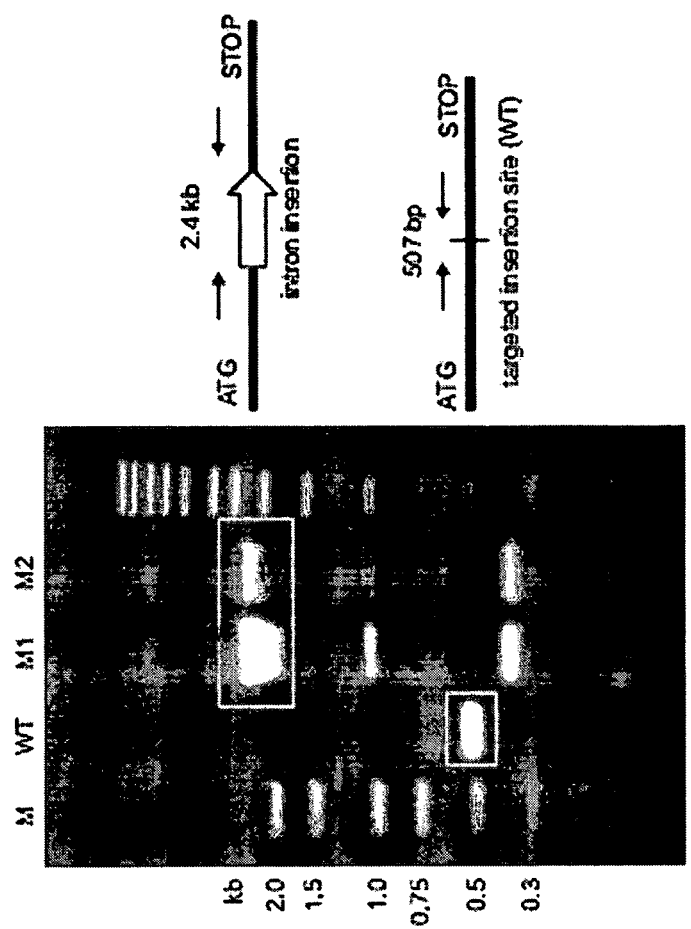
FIG. 1 depicts an image of a gel illustrating that the group II intron inserted at nucleotide 1259 of the E. coli rne gene. A schematic of the gene before and after insertion is shown at the right. Small arrows denote gene-specific PCR primers. A 507 bp band was amplified in the wild type (WT) cells and a 2.4 kb band was amplified in two isolates (M1, M2) of the MS1259 mutant RNase E cells. M denotes molecular size standards.

C-terminal truncations of RNase E typically decrease the protein's ability to degrade mRNA, thereby increasing mRNA stability, and consequently allowing increased protein translation. This is particularly useful in exogenous protein expression systems, whether based on bacterial systems, or cell-free systems. RNase E, however, is also involved in rRNA and tRNA processing, two essential steps preceding protein translation. If RNase E's ability to process rRNA and tRNA are disturbed, the rate of protein translation will decrease due to a lack of mature rRNA or tRNA. Therefore, it is believed that the present invention provides an RNase E polypeptide possessing exceptionally impaired ability to degrade mRNA, but retaining cell viability. Additionally, the current invention encompasses a bacterial strain comprising an RNase E polypeptide possessing impaired ability to degrade mRNA, but retaining cell viability. Furthermore, the invention encompasses methods for using the bacterial strain for exogenous protein production.

I. RNase E Polypeptides

One aspect of the invention, therefore, is an RNase E polypeptide that allows increased protein translation when compared to the wild-type RNase E protein. In one embodiment, the RNase E polypeptide has an amino acid sequence that is at least 45 percent identical to the first 459 amino acids of wild-type RNase E (SEQ ID NO:1). In another embodiment, the polypeptide has an amino acid sequence that is at least 50, 55, 60 or 65 percent identical to SEQ ID NO:1. In yet another embodiment, the polypeptide has an amino acid sequence that is at least 70, 75, 80, or 85 percent identical to SEQ ID NO:1. In still another embodiment, the polypeptide has an amino acid sequence that is at least 90, 91, 92 or 93 percent identical to SEQ ID NO:1. In still yet another embodiment, the polypeptide has an amino acid sequence that is at least 94, 95, 96, or 97 percent identical to SEQ ID NO:1. In a further embodiment, the polypeptide has an amino acid sequence that is at least 97, 98 or 99 percent identical to SEQ ID NO:1. In yet a further embodiment, the polypeptide has an amino acid sequence consisting of the first 420 amino acids of wild-type RNase E and six amino acids coded by the intron (SEQ ID NO:2). Wild-type Rnase E has an amino acid sequence consisting of SEQ ID NO:3.

Each polypeptide of the above embodiments typically possesses impaired mRNA degrading activity and typically possesses efficient rRNA and tRNA processing ability to facilitate increased protein translation when compared to wild-type RNase E. Such a comparison may be performed as described below and in Example 3. Additionally, the invention encompasses post-translational modifications to any of the above polypeptides of the invention. Post-translation modifications may be natural or synthetic. Non-limiting examples of post-translational modifications include glycosylation, phosphorylation, acetylation, alkylation, sulfation, ubiquitination, lipidation, carboxylation, and biotinylation.

In certain aspects, a polypeptide that is a homolog, ortholog, or degenerative variant of an RNase E polypeptide of the invention is also suitable for use in the present invention. Typically, the subject polypeptides include fragments that share substantial sequence similarity and functionality with an RNase E polypeptide of the invention. In particular, the subject polypeptide will typically possess decreased ability to degrade mRNA, and will typically possess efficient ability to process rRNA and tRNA, such that protein translation is increased when compared to wild-type RNase E.

A number of methods may be employed to determine whether a particular homolog or degenerative variant possesses substantially similar biological activity relative to the RNase E polypeptides of the invention. For instance, quantitative RT-PCR, may be used to determine the stability of known RNase E substrates in comparison to an RNase E polypeptide of the invention, as detailed in Example 2, and levels of protein production may be compared as in Example 3.

In addition to having a substantially similar biological function, a homolog or degenerative variant suitable for use in the invention will also typically share substantial sequence similarity to an RNase E polypeptide of the invention. Generally speaking, the subject polypeptide generally will possess tRNA and rRNA processing capabilities, and impaired mRNA processing ability. Typically, sequence differences between a selected homolog or variant and an RNase E polypeptide of the invention will include a number of conservative amino acid substitutions. A "conservative substitution" is a substitution that does not abolish the ability of a subject polypeptide to participate in tRNA or rRNA processing, or restore the polypeptides ability to participate in mRNA processing. In one embodiment, the present invention encompasses an RNase E polypeptide consisting essentially of SEQ ID NO:1 with from about 1 to about 50 conservative amino acid substitutions. In another embodiment, the polypeptide has from about 1 to about 40 conservative amino acid substitutions. In yet another embodiment, the polypeptide has from about 1 to about 30 conservative amino acid substitutions. In still yet another embodiment, the polypeptide has from about 1 to about 20 conservative amino acid substitutions. In a further embodiment, the polypeptide has from about 1 to about 10 conservative amino acid substitutions.

In determining whether a polypeptide is substantially identical to an RNase E polypeptide of the invention, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the NBLAST and XBLAST programs of Altschul et al. (J. Mol. Biol. 215:403-410, 1990). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are employed. See http://www.ncbi.nlm.nih.gov for more details.

RNase E polypeptides suitable for use in the invention may be isolated or pure. An "isolated" polypeptide is unaccompanied by at least some of the material with which it is associated in its natural state, preferably constituting at least about 0.5%, and more preferably, at least about 5% by weight of the total polypeptide in a given sample. A pure polypeptide constitutes at least about 90%, preferably, 95% and even more preferably, at least about 99% by weight of the total polypeptide in a given sample.

The RNase E polypeptide of the invention may be synthesized, produced by recombinant technology, or purified from cells. In one embodiment, an RNase E polypeptide of the present invention may be obtained by direct synthesis. In addition to direct synthesis, the subject polypeptides may also be expressed in cell and cell-free systems (e.g. Jermutus L, et al., Curr Opin Biotechnol. October 1998; 9(5):534-48) from encoding polynucleotides, such as described below. In other embodiments, any of the molecular and biochemical methods known in the art are available for biochemical synthesis, molecular expression and purification of an RNase E polypeptide of the invention, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York).

II. RNase E Encoding Nucleic Acids

Another aspect of the present invention is nucleotide sequences encoding an RNase E polypeptide of the invention. The subject nucleotide sequences may be utilized as a means to produce an RNase E polypeptide of the invention having the structure and biological activity detailed above.

The nucleotide sequence may be any of a number of such nucleotide sequences that encode a suitable RNase E polypeptide of the invention, as described herein. For example, a nucleotide sequence encoding the polypeptide sequence of SEQ ID NO:1 may be employed. In other embodiments, the nucleotide sequence of SEQ ID NO:8 may be employed. In yet other embodiments, the nucleotide sequence of SEQ ID NO:4 may be used.

The invention also encompasses the use of nucleotide sequences other than those specifically identified herein to the extent they encode an RNase E polypeptide of the invention having the structure and function described above. The invention also encompasses the use of a nucleotide sequence that will hybridize under stringent hybridization conditions (as defined herein) to all or a portion of a nucleotide sequence that encodes an RNase E polypeptide of the invention or its complement. The hybridizing portion of the hybridizing nucleic acids is usually at least 15 (e.g., 20, 25, 30, or 50) nucleotides in length. The hybridizing portion of the hybridizing nucleic acid is at least 80%, preferably, at least 90%, and is more preferably, at least 95% or 97% to 99% identical to the sequence of a portion or all of a nucleic acid sequence encoding an RNase E polypeptide suitable for use in the present invention, or its complement.

Hybridization of the oligonucleotide probe to a nucleic acid sample is typically performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming a 1% mismatching results in a 1° C. decrease in the Tm, the temperature of the final wash in the hybridization reaction is reduced accordingly. For example, if sequences having greater than 95% identity with the probe is sought, the final temperature is decreased by approximately 5° C. In practice, the change in Tm may be between 0.5 and 1.5° C. per 1% mismatch. Stringent conditions involve hybridizing at 68° C. in 5×SSC/5× Denhardt's solution/1.0% SDS, and washing in 0.2×SSC/0.1% SDS at room temperature. Moderately stringent conditions include washing in 3×SSC at 42° C. The parameters of salt concentration and temperature may be varied to achieve the optimal level of identity between the probe and the subject nucleotide sequence. Additional guidance regarding such conditions is readily available in the art, for example, by Sambrook et al., 1989, Molecular Cloning, A Laboratory Manual, Cold Spring Harbor Press, N.Y.; and Ausubel et al., (eds.), 1995, Current Protocols in Molecular Biology, (John Wiley & Sons, N.Y.) at Unit 2.10.

The various nucleic acid sequences mentioned above may be obtained using a variety of different techniques known in the art. The nucleotide sequences, as well as homologous sequences encoding an RNase E polypeptide, may be isolated using standard techniques, or may be purchased or obtained from a depository. Once the nucleotide sequence is obtained, it may be amplified for use in a variety of applications, as further described below.

The invention also encompasses production of nucleotide sequences that encode RNase E homologs, derivatives, or fragments thereof, having the RNA processing activity described above, that may be made by any method known in the art, including by synthetic chemistry. After production, the synthetic sequence may be inserted into any of the many available expression vectors and cell systems using reagents well known in the art. Alternatively, synthetic chemistry may be used to introduce mutations into a nucleotide sequence encoding an RNase E polypeptide of the invention.

The nucleotide sequences of the present invention may be engineered using methods generally known in the art in order to alter RNase E polypeptide-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

III. Expression of RNase E Polypeptides

In order to express a biologically active RNase E polypeptide of the invention, the nucleotide sequences encoding such polypeptides may be inserted into an appropriate expression vector. An "appropriate vector" is typically a vector that contains the necessary elements for transcriptional and translational control of the inserted coding sequence in a suitable host. These elements generally will include regulatory sequences, such as enhancers, constitutive and inducible promoters, and 5' and 3' untranslated regions in the vector and in polynucleotide sequences encoding RNase E polypeptides of the invention. Such elements may vary in their strength and specificity. Specific initiation signals may also be used to achieve more efficient translation of nucleotide sequences encoding RNase E polypeptides of the invention. These signals, for example, include the ATG initiation codon and adjacent sequences (e.g. the Kozak sequence). In cases where nucleotide sequences encoding the subject polypeptide and its initiation codon and upstream regulatory sequences are inserted into the appropriate expression vector, no additional transcriptional or translational control signals may be needed. But in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (See, e.g., Scharf, D. et al. (1994) Results Probl. Cell Differ. 20:125-162).

Methods that are well known to those skilled in the art may be used to construct expression vectors containing sequences encoding the RNase E polypeptide of the invention and appropriate transcriptional and translational control elements. These methods include, for example, in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview N.Y., ch. 4, 8, and 16-17; Ausubel, F. M. et al. (1995) Current Protocols in Molecular Biology, John Wiley & Sons, New York N.Y., ch. 9, 13, and 16).

It is also contemplated that a variety of expression vector/host systems may be utilized to contain and express nucleotide sequences encoding polypeptides of the invention. By way of non limiting example, these include microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. (1987) EMBO J. 6:307-311; The McGraw Hill Yearbook of Science and Technology (1992) McGraw Hill, New York N.Y., pp. 191-196; Logan, J. and T. Shenk (1984) Proc. Natl. Acad. Sci. USA 81:3655-3659; and Harrington, J. J. et al. (1997) Nat. Genet. 15:345-355).

Any number of selection systems may be used to recover transformed cell lines. These include, but are not limited to, the herpes simplex virus thymidine kinase and adenine phosphoribosyltransferase genes, for use in tk- and apr-cells, respectively. (See, e.g., Wigler, M. et al. (1977) Cell 11:223-232; Lowy, I. et al. (1980) Cell 22:817-823.) Also, antimetabolite, antibiotic, or herbicide resistance may be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively. (See, e.g., Wigler, M. et al. (1980) Proc. Natl. Acad. Sci. USA 77:3567-3570; Colbere-Garapin, F. et al. (1981) J. Mol. Biol. 150:1-14). Additional selectable genes have been described, e.g., trpB and hisD, which alter cellular requirements for metabolites. (See, e.g., Hartman, S.C. and R. C. Mulligan (1988) Proc. Natl. Acad. Sci. USA 85:8047-8051). Visible markers, e.g., anthocyanins, green fluorescent proteins (GFP; Clontech), β-glucuronidase and its substrate β-glucuronide, or luciferase and its substrate luciferin may be used. These markers may be used not only to identify transformants, but also to quantify the amount of transient or stable protein expression attributable to a specific vector system. (See, e.g., Rhodes, C. A. (1995) Methods Mol. Biol. 55:121-131).

Although the presence/absence of marker gene expression suggests that the nucleotide sequence of interest is also present, the presence and expression of the gene may need to be confirmed. For example, if the sequence encoding an RNase E polypeptide of the invention is inserted within a marker gene sequence, transformed cells containing the subject polypeptide may be identified by the absence of marker gene function. Alternatively, a marker gene may be placed in tandem with a sequence encoding an RNase E polypeptide of the invention under the control of a single promoter. Expression of the marker gene in response to induction or selection usually indicates expression of the tandem gene as well.

Generally speaking, host cells that contain the nucleotide sequence encoding RNase E polypeptides of the invention may be identified by a variety of procedures known to those of skill in the art. These procedures include, but are not limited to, DNA-DNA or DNA-RNA hybridizations, PCR amplification, and protein bioassay or immunoassay techniques that include membrane, solution, or chip based technologies for the detection and/or quantification of nucleic acid or protein sequences.

By way of example, immunological methods for detecting and measuring the expression of RNase E polypeptides using either specific polyclonal or monoclonal antibodies are known in the art. Examples of such techniques include enzyme-linked immunoabsorbent assays (ELISAs), radioimmunoassays (RIAs), and fluorescence activated cell sorting (FACS). (See, e.g., Hampton, R. et al. (1990) Serological Methods, a Laboratory Manual, APS Press, St. Paul Minn., Sect. IV; Coligan, J. E. et al. (1997) Current Protocols in Immunology, Greene Pub. Associates and Wiley-Interscience, New York N.Y.; and Pound, J. D. (1998) Immunochemical Protocols, Humana Press, Totowa N.J).

Host cells transformed with nucleotide sequences encoding RNase E polypeptides may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing the subject nucleotide sequence may be designed to contain signal sequences that direct secretion of RNase E polypeptides of the invention through a prokaryotic or eukaryotic cell membrane.

In addition, a host cell strain may be chosen for its ability to modulate expression of the inserted nucleotide sequences or to process the expressed protein in the desired fashion. Such modifications of the polypeptide include, but are not limited to, acetylation, carboxylation, glycosylation, phosphorylation, lipidation, and acylation. Different host cells that have specific cellular machinery and characteristic mechanisms for post-translational activities (e.g., CHO, HeLa, MDCK, HEK293, and W138) are available from the American Type Culture Collection (ATCC, Manassas Va.) and may be chosen to ensure the correct modification and processing of the foreign protein.

IV. Bacterial Strains

A further aspect of the invention encompasses a bacterial strain with a chromosomally integrated nucleotide sequence that encodes an RNase E polypeptide of the invention. The RNase E polypeptide, as described above, typically has decreased mRNA degrading ability, and typically has efficient rRNA and tRNA processing activity. This combination, as illustrated in the examples, allows increased exogenous protein production when compared to wild-type RNase E. This comparison may be made in any number of ways by one of skill in the art and is generally done under comparable growth conditions. For example, the amount of exogenous protein produced may be quantified and compared by preparing protein extracts from the cells, subjecting them to SDS-PAGE, transferring them to a Western blot, then detecting the exogenous protein with specific antibodies. Alternatively, the exogenous protein may be biotinylated, and therefore, detected using kits which are commercially available from, for example, Pierce Chemical Company (Rockford, Ill.), Sigma Chemical Company (St. Louis, Mo.) or Boehringer Mannheim (Indianapolis, Ind.) for visualizing biotinylated proteins on Western blots. In another alternative, the level of exogenous protein produced compared to wild-type may be measured as explained in Example 3.

As will be appreciated by a skilled artisan, the nucleic acid sequence encoding an RNase E polypeptide of the invention may be chromosomally integrated into a variety of suitable bacterial hosts, from which the endogenous RNase E gene has been deleted. By way of non limiting example, the nucleic acid sequence encoding a RNase E polypeptide of the invention may be chromosomally integrated into a bacterial species selected from the following: *E. coli, Streptomyces, Rhodobacter, Salmonella, Shigella, Bacillus*, and *Influenza*. In another embodiment, the bacterial species is *Influenza* or *Bacillus*. In yet another embodiment, the bacterial species is *Salmonella* or *Shigella*. In still yet another embodiment, the bacterial species is *Streptomyces* or *Rhodobacter*. In an exemplary embodiment, the bacterial species is *E. coli*. Because of the ubiquitous nature of RNase E proteins, it will be appreciated by those skilled in the art that additional bacterial species other than the ones specifically detailed herein may be used without departing from the scope of the invention.

The nucleic acid sequence of the invention may be chromosomally integrated into the bacterial strain through a variety of means. For example, an exogenous sequence may be introduced to the bacterial strain and subsequently integrated into the chromosome, or, the wild type RNase E sequence of the bacterium may be altered to create a nucleic acid sequence that encodes an RNase E polypeptide of the invention. Methods of chromosomally integrating a nucleic acid sequence of the invention are known in the art. Non-limiting examples include methods employing recombination or insertion techniques.

Nucleic acid sequences, whether heterologous or endogenous with respect to the host cell, may be introduced into a bacterial chromosome using, for example, homologous recombination. Homologous recombination, in general, involves inserting the gene of interest and a marker gene into a plasmid that contains a piece of DNA that is homologous to the region of the chromosome within which the gene of interest is to be inserted. Next this recombinagenic DNA is introduced into the bacteria, and clones are selected in which the DNA fragment containing the gene of interest and marker have recombined into the chromosome at the desired location. The gene and marker may be introduced into the bacteria via transformation either as a linearized piece of DNA that has been prepared from any cloning vector, or as part of a specialized recombinant suicide vector that cannot replicate in the bacterial host. In the case of linearized DNA, a recD⁻ host may optionally be used to increase the frequency at which the desired recombinants are obtained. Clones are then verified using PCR and primers that amplify DNA across the region of insertion.

Insertion techniques for chromosomal integration generally employ a means to specifically insert the desired nucleic acid sequence. Viruses, including bacteriophages such as lambda phage, may be used to insert a desired sequence into a bacterial chromosome. Additionally, transposons may be used to insert a desired sequence into a bacterial chromosome. Preferably, the insertion is directed, as opposed to random.

Additionally, insertions may also be used to disrupt a wild-type RNase E sequence to create a chromosomal nucleic acid sequence of the invention. A detailed example of using a targeted group II intron to create a chromosomal nucleic acid sequence of the invention is described in Example 1. Briefly, a retrotransposon comprising a group II intron is modified by PCR such that its insertion is directed to a specific desired location. The desired location is chosen so as to disrupt the gene of interest. The bacteria are transformed with as vector carrying the modified group II intron, which inserts in the desired chromosomal location. The insertion of the intron disrupts the targeted gene, creating a novel chromosomal nucleic acid sequence. (See U.S. Pat. Nos. 5,698,421; 5,804,418; 5,869,634; 6,027,895; 6,001,608; and 6,306,596 which are hereby incorporated by reference.) In this case, the inserted group II intron creates a sequence that encodes an RNase E polypeptide of the invention.

Alternatively, in a less preferred embodiment, an RNase E nucleotide sequence of the invention may be introduced into a bacterial strain by a method not involving chromosomal integration. In this embodiment, the bacterial strain may be transformed with an RNase E nucleotide sequence of the invention. The nucleotide sequence may be incorporated in a plasmid. The bacterial strain may or may not have a chromosomal RNase E nucleotide sequence. Additionally, the bacterial strain may be recombination deficient. Appropriate plasmids and methods of transformation are well known in the art.

V. Exogenous Protein Production in Bacterial Strains of the Invention

Bacterial strains of the present invention may be used in methods for exogenous protein production systems. Generally speaking, these systems employ the transcriptional and translational systems of a bacterium of the invention to over-produce an exogenous protein of interest. As will be appreciated by a skilled artisan, protein production systems typically entail transforming a competent bacteria strain of the invention with an expression vector encoding the protein of interest, growing the bacteria under conditions that support the production of the protein of interest, and purifying the protein of interest from the bacterial cells and/or culture media.

A variety of methods are suitable for transforming a bacterial strain of the present invention with an expression vector. Common bacterial transformation methods include electroporation, liposomal mediated transformation, calcium mediated transformation, and viral mediated transfection. In one embodiment, the bacterial cells of the invention are electroporated. In another embodiment, the bacterial cells are transformed with liposomes. In yet another embodiment, the bacterial cells are transformed with calcium. In still another embodiment, the bacterial cells are transformed with a virus.

Plasmids for exogenous protein production are well known in the art (Makrides, Strategies for Achieving High-Level Expression of Genes in *Escherichia Coli, Microbio Reviews*, 1996, v. 60(3) pg. 512-38). Briefly, a variety of cloning and expression vectors may be selected depending upon the protein of interest and its intended use. When large quantities of polypeptide are needed, vectors that direct high level expression of the protein of interest may be used. For example, vectors containing the strong, inducible SP6 or T7 bacteriophage promoter may be used for this embodiment. Preferably, the nucleic acid fragment is introduced into the cell using an expression vector, although "naked DNA" may also be used. The nucleic acid fragment may be circular or linear, single-stranded or double stranded, and may be DNA, RNA, or any modification or combination thereof. The expression vector may be a plasmid, a viral vector or a cosmid. Selection of a vector or plasmid backbone depends upon a variety of desired characteristics in the resulting construct, such as a selection marker, plasmid reproduction rate, and the like. Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors may be obtained from Pharmacia Biotech (Piscataway, N.H.) or Sigma Chemical Co. (St. Louis, Mo.). pKK223-3, pKK233-2 and pTrc99A may be obtained from Pharmacia Biotech. pET-(X) vectors may be obtained from Promega (Madison, Wis.), Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

The nucleic acid fragment used to transform the bacterial cell according to the invention may optionally include a promoter sequence operably linked to the nucleotide sequence encoding the target protein to be expressed in the bacterial cell. The invention is not limited by the use of any particular promoter, and a wide variety of promoters are known. Promoters act as regulatory signals that bind RNA polymerase in a cell to initiate transcription of a downstream (3' direction)

coding sequence. The promoter used in the invention may be a constitutive or an inducible promoter. It may be, but need not be, heterologous with respect to the host cell. Preferred promoters for the expression vector include tac, trc, T7, lambda PL and araBAD. In one embodiment, the promoter is tac. In another embodiment, the promoter is trc. In yet another embodiment, the promoter is T7. In an additional embodiment, the promoter is lambda PL. In an alternative embodiment, the promoter is araBAD.

The nucleic acid fragment used to transform the host cell may, optionally, include a Shine Dalgarno site (e.g., a ribosome binding site) and a start site (e.g., the codon ATG) to initiate translation of the transcribed message to produce the enzyme. It may, also optionally, include a termination sequence to end translation. A termination sequence is typically a codon for which there exists no corresponding aminoacetyl-tRNA, thus ending polypeptide synthesis. The nucleic acid fragment used to transform the host cell may optionally include a transcription termination sequence. The rrnB terminators, which is a stretch of DNA that contains two terminators, T1 and T2, is the most commonly used terminator that is incorporated into bacterial expression systems (J. Brosius et al., J. Mol. Biol., 148, 107-127 (1981)).

In a further embodiment, use of an inducible transcription initiation region is contemplated. In this manner, the host strain may be grown to high density prior to significant expression of the desired product. Providing for inducible transcription is particularly useful where the peptide is retained in the cellular host rather than secreted by the host. A number of inducible transcription initiation regions are suitable for use in the present invention. The inducible regions may be controlled by a particular chemical, such as isopropyl thiogalactoside (IPTG). Other inducible regions include lambda left and right promoters; various amino acid polycistrons, e.g., histidine and tryptophan; temperature sensitive promoters; and regulatory genes, e.g., $ci^{ts\ 857}$.

The nucleic acid fragment used to transform the host cell optionally may include one or more marker sequences. Generally speaking, suitable marker sequences typically encode a gene product, usually an enzyme that inactivates or otherwise detects or is detected by a compound in the growth medium. For example, the inclusion of a marker sequence may render the transformed cell resistant to an antibiotic, or it may confer compound-specific metabolism on the transformed cell. Examples of a suitable marker sequences that confer resistance include kanamycin, ampicillin, chloramphenicol and tetracycline. Alternatively, rather than selective pressure, a marker gene may be used that allows for detection of particular colonies containing the gene, such as beta-galactosidase, where a substrate is employed that provides for a colored product.

Following the introduction of the vector, bacterial cells may be grown for about 1 to 2 days in enriched media. Alternatively, the cells may be switched to selective media. The purpose of the selectable marker is to confer resistance to a selective agent, and its presence allows growth and recovery of cells that successfully express the introduced sequences. Resistant clones of stably transformed cells may be propagated using tissue culture techniques appropriate to the cell type.

After growth of the transformants or integrants to high density in an appropriate nutrient medium, transcription is induced in accordance with the nature of the transcriptional system of the expression construct. Where the desired protein is retained in the cytoplasm, these cells are harvested and lysed, and, depending upon the use of the protein, the protein may be further purified in accordance with conventional techniques, such as chromatography (including size exclusion, ion exchange, and high performance liquid chromatography), solvent extraction, affinity chromatography, centrifugal sedimentation, filtration and the like. In one embodiment, the protein is purified by chromatography. In another embodiment, the protein is purified by solvent extraction. In still another embodiment, the protein is purified by centrifugal sedimentation. In an additional embodiment, the protein is purified by filtration.

VI. Kits of the Invention

A further aspect of the invention encompasses a kit comprising the bacterial strain of the invention, as described above, and instructions for producing exogenous protein. In one embodiment, the bacterial strain is competent. In another embodiment, the kit comprises sterile media for use in growing the bacterial strain of the invention. In yet another embodiment, the kit comprises an expression vector. The expression vector comprises an insertion site for the exogenous protein. In still yet another embodiment, the expression vector of the kit comprises an inducible expression vector. In a further embodiment, the inducible expression vector comprises an inducible promoter. In an additional embodiment, the inducible promoter is selected from the group consisting of tac, trc, T7, lambda PL and araBAD. In one embodiment, the promoter is tac. In another embodiment, the promoter is trc. In yet another embodiment, the promoter is T7. In an additional embodiment, the promoter is lambda PL. In an alternative embodiment, the promoter is araBAD.

Definitions

"Conservative" amino acid substitutions are those substitutions that typically do not substantively abolish the ability of a subject polypeptide to participate in the biological functions as described herein. Typically, a conservative substitution will involve a replacement of one amino acid residue with a different residue having similar biochemical characteristics such as size, charge, and polarity versus non polarity. A skilled artisan may readily determine such conservative amino acid substitutions.

"Efficient ability to process" mRNA and tRNA is used herein as a means to compare the relative rRNA and tRNA processing abilities of an RNase E polypeptide of the invention, wild-type RNase E, and other chromosomally integrated RNase E mutations. Such a comparison may be made by measuring protein translation as described herein and in Example 3.

"Exogenous" is used herein to refer to any protein whose nucleotide sequence is introduced into a bacterial strain in an expression vector, such as a plasmid. For instance, an E. coli protein whose nucleotide sequence is introduced into an E. coli cell on a plasmid would be an exogenous protein as used herein.

"Impaired mRNA degrading activity" is used herein as a means to compare the relative mRNA degrading abilities of an RNase E polypeptide of the invention and wild-type RNase E. Such a comparison may be made by measuring mRNA stability using a quantitative RT-PCR reaction as described in Example 2.

"Homology" describes the degree of similarity in nucleotide or protein sequences. When referring to the homology between either two proteins or two nucleotide sequences, homology refers to molecules having substantially the same function, but differing in sequence. Most typically, the two homologous molecules will share substantially the same sequence, particularly in conserved regions, and will have sequence differences in regions of the sequence that does not impact function.

"Wild-type" is the most frequently observed phenotype, or the one arbitrarily designated as "normal". As used herein, wild-type RNase E has SEQ ID NO:3.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Disruption of the Chromosomal rne Gene of E. Coli Using the TargeTron™ Gene Knockout System Mutations were introduced by PCR at several locations in the group II intron from *Lactococcus lactis* so that it would re-target to the rne gene (SEQ ID NO:3) of *E. coli*. Three rne targeting primers were designed (Table 1) so that the intron would insert at nucleotide 1259 of the rne gene. The three rne targeting primers and an EBS universal primer were combined in a single-tube reaction to mutate the intron at several positions spanning a 350 bp region. Duplicate reactions were assembled containing 23 μl of PCR-grade H$_2$O, 1 μl of the 4-primer mix (containing 10 μM IBS½ primer, 10 μM EBS1d primer, 2 μM EBS2 primer, and 2 μM EBS universal primer), 1 μl of Intron PCR template, and 25 μl of JumpStart REDTaq ReadyMix (Product No. P0982). The reactions were denatured at 94° C. for 2 min. and cycled 30 times at 94° C. for 15 sec, 55° C. for 30 sec, and 72° C. for 30 sec. After a final extension at 72° C. for 2 min, they were kept at 4° C. Aliquots (8 μl) of the reaction mixture were run on a 4% agarose gel to confirm a product of the expected size. The 350 bp re-targeting intron PCR product was purified and digested with HindIII and BsrGI at 37° C. for 30 min and 60° C. for 30 min; the reaction was terminated by incubation at 80° C. for 10 min. The 350 bp Hind III/BsrG I-digested intron PCR product (7 μl) was ligated with the pACD4K-C linear vector (20 ng) using the Quick-Link T4 DNA Ligation Kit (Product No. LIG-2).

*E. coli* BL21 (DE3)-T1$^R$ cells (Product No. B2935) were transformed with the ligation mix using standard procedures and incubated overnight with shaking at 37° C. in LB medium containing 25 mg/ml chloramphenicol, 1% glucose. An aliquot (40 μl) of the overnight culture was diluted in 2 ml of LB medium containing 25 mg/ml chloramphenicol, 1% glucose and grown at 37° C. to an OD$_{600}$ of approximately 0.2. To induce expression of the inserted intron, 10 μl of 100 mM IPTG was added and the culture was incubated at 30° C. for 30 min with shaking. The cells were immediately spun at maximum speed in a microcentrifuge for 1 min and resuspended in 1 ml of LB medium containing 1% glucose (no chloramphenicol). The cells were incubated for 1 hr at 30° C. with shaking, and aliquots (100 μl) were spread on LB agar plates containing 25 μg/ml kanamycin. The plates were incubated at 30° C. (or room temperature) for several days.

Colonies were picked and colony PCR was performed to verify the correct target site insertion. First, rne gene-specific primers that flank the insertion site and amplify the entire inserted intron were used. FIG. 1 shows that these primers amplified a 507 bp product in the wild type (WT) BL21(DE3) cells and a 2.4 kb product in two colonies (M1, M2) with group II intron insertions. Second, gene-specific and intron-specific primers that amplify across the intron-gene junctions were used to verify the insertion. Products of the expected sizes (603 bp at the 5' junction and 732 bp at the 3' junction) were generated. Sequence analyses verified that the intron inserted at nucleotide 1259 of the rne gene; the entire rne::intron1259 ORF is 5475 bp in length (SEQ ID NO:4). The size of the mutant RNase E protein is predicted to be 426 amino acids, with the first 420 amino acids identical to the wildtype RNase E and the last 6 amino acids coded by the intron (SEQ ID NO:2). The cells carrying this mutant version of RNase E are called MS1259 cells.

TABLE 1

The primers used to create mutations in the group II intron of *L. lactis*.

| Primer name | Sequence | SEQ ID NO: |
|---|---|---|
| IBS1/2 | AAAAAAGCTTATAATTATCCTTACGAATCGCTGTCGT GCGCCCAGATAGGGTG | 5 |
| EBS1d | CAGATTGTACAAATGTGGTGATAACAGATAAGTCGCT GTCGCTAACTTACCTTTCTTTGT | 6 |
| EBS2 | TGAACGCAAGTTTCTAATTTCGGTTATTCGTCGATAG AGGAAAGTGTCT | 7 |

Example 2

Increased rpsT and rpsO Transcript Stability in the MS1259 Strain

Transcripts of the rpsT and rpsO genes, which code for the ribosomal proteins S20 and S15, respectively, are known substrates of RNase E. Two MS1259 insertional mutant isolates (2-1-2 and 2-2-4) and wild type BL21(DE3) cells were grown to mid-log phase (OD$_{600}$~0.6). Total RNA was isolated using Sigma's Bacterial Total RNA isolation kit. To remove any contaminating genomic DNA, the RNA samples were treated with DNase I using Sigma's AMPD-1 kit. The amount of input total RNA was normalized for each sample. Quantitative RT-PCR (qRT-PCR) was performed in duplicate using gene specific primers for rpsT or rpsO and the SYBR Green qRT-PCR kit (Product No. QRO100) in a MX3000P (Statagene) quantitative PCR instrument.

Figure 2:
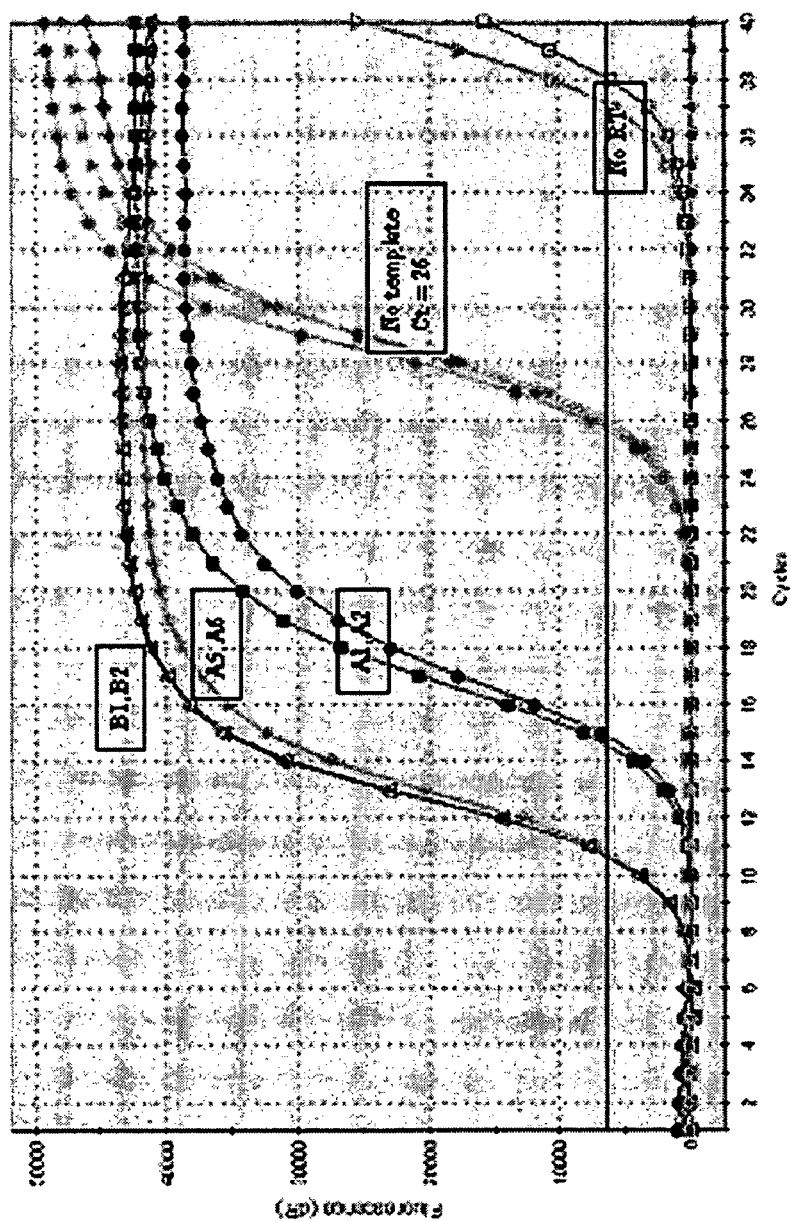
FIG. 2 depicts a qRT-PCR plot illustrating the increased levels of rpsT mRNA in the MS1259 mutant RNase E cells. Amplification plots are shown for two MS1259 isolates (B1, B2 and A5, A6) and wild type BL21 (DE3) cells (A1, A2). Also shown are curves with no template added or no reverse transcriptase (RT) added.
Figure 3:
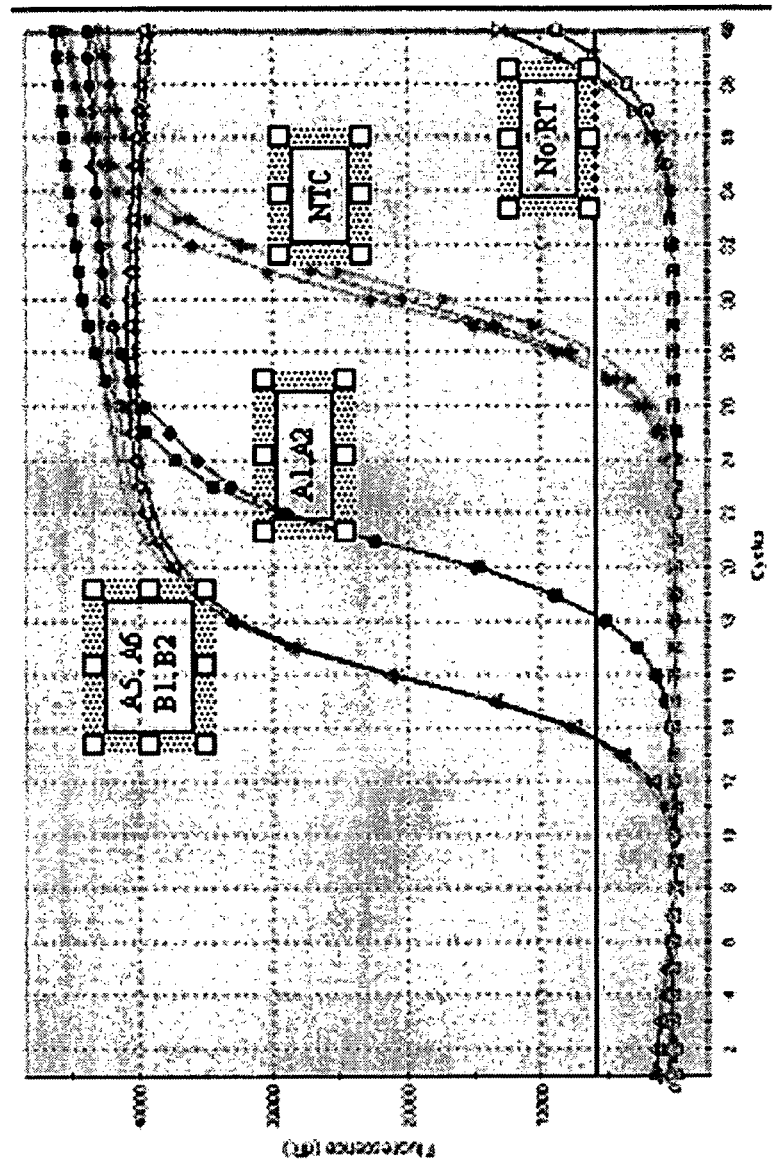
FIG. 3 depicts a qRT-PCR plot illustrating the increased levels of rpsO mRNA in the MS1259 mutant cells. Amplification plots are shown for two MS1259 isolates (A5, A6 and B1, B2) and wild type BL21(DE3) cells (A1, A2). Also shown are curves with no template (NTC) added or no reverse transcriptase (RT) added.

FIG. 2 presents the results for the rpsT mRNA. The mean threshold cycle (Ct) value for the wild type cells (A1, A2) was 14.7 cycles, whereas the mean Ct value for the two MS1259 mutant isolates, 2-1-2 (A5, A6) and 2-2-4 (B1, B2), were 10.7 and 10.6 cycles, respectively. Since the difference in Ct values (ΔCt) was 4, the difference in RNA levels between the two conditions is 16-fold ($2^4$=16). Thus, the MS1259 mutant cells had 16-fold higher levels of rpsT mRNA. FIG. 3 shows the qRT-PCR data for the rpsO transcript. The mean Ct value for the wild type cells (A1, A2) was 18.2 cycles, whereas the mean Ct value for the two mutant isolates, 2-1-2 (A5, A6) and 2-2-4 (B1, B2), were 13.4 and 13.6 cycles, respectively. This experiment reveals that the MS1259 mutant cells had 26-fold higher levels of rpsO mRNA (ΔCt=4.7; $2^{4.7}$=26) than the wild type cells.

Figure 4:
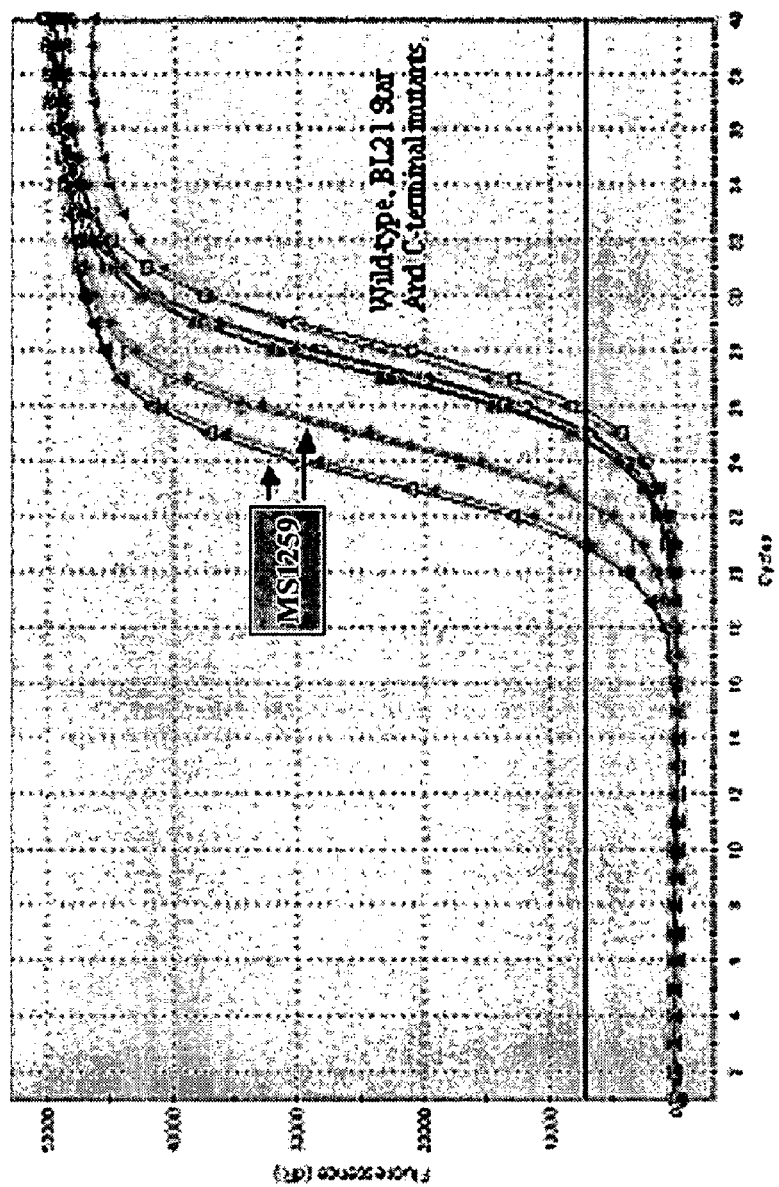
FIG. 4 depicts a qRT-PCR plot illustrating that the MS1259 mutant cells have increased levels of rpsO mRNA as compared to wild type and other RNase E mutant cells.

The stability of the rpsO transcript was also compared in the MS1259 mutant cells and a commercially available strain of RNase E mutant cells in which the C-terminal 477 amino acids are missing (BL21 Star (DE3) or BL21(DE3) rne131 cells; Invitrogen). Total RNA was isolated from two separate cultures of the MS1259 isolate (2-2-4) on different days. Total RNA was also isolated from wild type BL21(DE3) cells, BL21 Star (DE3) cells; and several other C-terminal RNase E mutants generated by the TargeTron™ Gene Knockout System (an intron was inserted at nucleotide 2256, 2670, or 2905). Quantitative RT-PCR was performed as described above. FIG. 4 presents a plot illustrating that the MS1259 mutant cells had increased levels of rpsO mRNA relative to all the other cells. (The mean Ct values were 25 cycles for the wild type BL21(DE3) cells, 21 and 22.5 cycles for two preparations of the MS1259 mutants, 24.7 cycles for the BL21 Star (DE3) cells, and 24.9-25.7 cycles for the other C-terminal RNase E mutants).

Example 3

Increased Expression of the LtrA Protein in the MS1259 Strain

Experiments were conducted to compare the expression of a recombinant fusion protein in the MS1259 RNase E mutant cells, wild type BL21(DE3) cells, and the BL21 Star (DE3) RNase E mutant cells (Invitrogen). Cells were transformed with a plasmid that expresses the LtrA protein from the *L. lactis* LtrB intron as a fusion with the chitin binding protein (CBD) and an intein domain. Single colonies were picked, cultured, and stored as glycerol stocks. Glycerol stocks were inoculated into 500 ml of LB medium containing 50 μg/ml ampicillin and grown to an $OD_{600}$ of ~0.6 at 37° C. with shaking at 250 rpm. The temperature was shifted to 25° C. and cells were induced with 0.5 mM IPTG for 6 hours. Cells were harvested by centrifugation at 3,000×g for 15 min and lysed by three cycles of freeze-thawing followed by sonication. The LtrA-CBP-intein protein was then purified as previously described (Saldanha et. al. Biochemistry 1999, 38, 9069-9083.). Fusion protein was eluted from chitin affinity columns and the LtrA protein was cleaved from the CBD-intein fusion using DTT.

Figure 5:
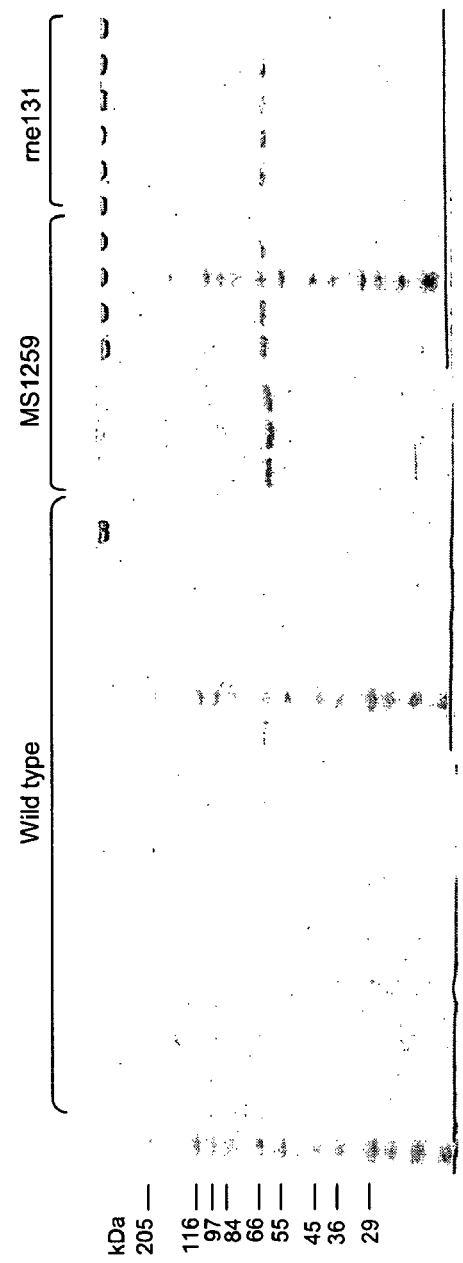
FIG. 5 displays an image of a protein gel containing sequential column fractions of the recombinant LtrA fusion protein purified from different strains of cells. The fusion protein was expressed and purified from wild type BL21 (DE3) cells, MS1259 RNase E mutant cells, and BL21 Star (DE3) rne131 mutant cells.

FIG. 5 presents Coomassie-stained protein gels containing sequential column fractions of LtrA protein purified from the different strains. The theoretical size of the LtrA protein is 70 kDa, but it typically runs at about 66 kDa. While the BL21 Star (DE3) mutant cells had increased levels of LtrA protein over wild type cells, the MS1259 RNase E mutant cells had even higher levels of LtrA protein. These data suggest that increased stability of transcripts in the MS1259 RNase E mutant cells, combined with efficient rRNA and tRNA processing, leads to increased protein production.

What is claimed is:

1. A bacterial strain, the strain having a chromosomally integrated nucleotide sequence consisting essentially of a sequence that encodes an RNase E polypeptide with an amino acid sequence that is identical to SEQ ID NO:1, wherein the polypeptide possesses impaired ability to degrade mRNA.

2. The bacterial strain of claim 1, wherein the polypeptide comprises post-translational modifications selected from the group consisting of glycosylation, phosphorylation, acetylation, alkylation, sulfation, ubiquitination, lipidation, carboxylation, biotinylation, and combinations thereof.

3. The bacterial strain of claim 1, wherein the bacterial strain has impaired mRNA degrading activity compared to a bacterial strain having a nucleotide sequence that encodes a polypeptide with an amino acid sequence comprising SEQ ID NO:3.

4. The bacterial strain of claim 1, wherein the bacterial strain is *E. coli*.

5. A method for enchancing production of an exogenous protein, the method comprising expressing the exogenous protein in a bacterial strain, the strain having a chromosomally integrated nucleotide sequence consisting essentially of a sequence that encodes an RNase E polypeptide with an amino acid sequence that is identical to SEQ ID NO:1, wherein the polypeptide possesses impaired ability to degrade mRNA.

6. The method of claim 5, wherein the polypeptide comprises post-translational modifications selected from the group consisting of glycosylation, phosphorylation, acetylation, alkylation, sulfation, ubiquitination, lipidation, carboxylation, biotinylation, and combinations thereof.

7. The method of claim 5, wherein the bacterial strain has impaired mRNA degrading activity compared to a bacterial strain having a nucleotide sequence that encodes a polypeptide with an amino acid sequence comprising SEQ ID NO:3.

8. The method of claim 5, further comprising transforming the bacterial strain with an expression vector, the vector comprising a nucleotide sequence encoding at least one exogenous protein.

9. The method of claim 5, further comprising transforming the bacterial strain with an exogenous inducible expression vector.

10. The method of claim 8, wherein the bacterial strain is transformed by a method selected from the group consisting of electroporation, liposomal mediated transformation, calcium mediated transformation, and viral mediated transfection.

11. The method of claim 9, wherein the exogenous inducible expression vector comprises a promoter selected from the group consisting of tac, trc, T7, lambda PL and araBAD.

12. The method of claim 5, further comprising culturing the bacterial cells under conditions sufficient to permit expression of the exogenous protein.

13. The method of claim 12, further comprising inducing the bacterial cells to express the exogenous protein.

14. The method of claim 5, further comprising purifying the exogenous protein from the bacterial cells.

15. The method of claim 14, wherein the exogenous protein is purified from the bacterial cells by a method selected from the group consisting of affinity purification, chromatography, solvent extraction, centrifugal sedimentation, and filtration.

16. A kit for producing an exogenous protein, the kit comprising:
   (a) a bacterial strain, the strain having a chromosomally integrated nucleotide sequence consisting essentially of a sequence that encodes an RNase E polypeptide with an amino acid sequence that is identical to SEQ ID NO:1, wherein the polypeptide possesses impaired ability to degrade mRNA; and
   (b) instructions for producing the exogenous protein.

17. The kit of claim 16, wherein the cells comprising the bacterial strain are competent.

18. The kit of claim 16, wherein the bacterial strain is *E. coli*.

19. The kit of claim 16, further comprising sterile media for growing the bacterial cells.

20. The kit of claim 16, further comprising an expression vector having an insertion site for the exogenous protein.

21. The kit of claim 20, wherein the expression vector is inducible.

22. The kit of claim 21, wherein the inducible expression vector comprises an inducible promoter.

23. The kit of claim 22, wherein the inducible promoter is selected from the group consisting of tac, trc, T7, lambda PL and araBAD.

* * * * *

SEQUENCE LISTING

```
<160> NUMBER OF SEQ ID NOS: 8

<210> SEQ ID NO 1
<211> LENGTH: 459
<212> TYPE: PRT
<213> ORGANISM: Escherichia coli

<400> SEQUENCE: 1

Met Lys Arg Met Leu Ile Asn Ala Thr Gln Gln Glu Glu Leu Arg Val
1               5                   10                  15

Ala Leu Val Asp Gly Gln Arg Leu Tyr Asp Leu Asp Ile Glu Ser Pro
            20                  25                  30

Gly His Glu Gln Lys Lys Ala Asn Ile Tyr Lys Gly Lys Ile Thr Arg
        35                  40                  45

Ile Glu Pro Ser Leu Glu Ala Ala Phe Val Asp Tyr Gly Ala Glu Arg
    50                  55                  60

His Gly Phe Leu Pro Leu Lys Glu Ile Ala Arg Glu Tyr Phe Pro Ala
65                  70                  75                  80

Asn Tyr Ser Ala His Gly Arg Pro Asn Ile Lys Asp Val Leu Arg Glu
                85                  90                  95

Gly Gln Glu Val Ile Val Gln Ile Asp Lys Glu Glu Arg Gly Asn Lys
            100                 105                 110

Gly Ala Ala Leu Thr Thr Phe Ile Ser Leu Ala Gly Ser Tyr Leu Val
        115                 120                 125

Leu Met Pro Asn Asn Pro Arg Ala Gly Gly Ile Ser Arg Arg Ile Glu
    130                 135                 140

Gly Asp Asp Arg Thr Glu Leu Lys Glu Ala Leu Ala Ser Leu Glu Leu
145                 150                 155                 160

Pro Glu Gly Met Gly Leu Ile Val Arg Thr Ala Gly Val Gly Lys Ser
                165                 170                 175

Ala Glu Ala Leu Gln Trp Asp Leu Ser Phe Arg Leu Lys His Trp Glu
            180                 185                 190
```

```
Ala Ile Lys Lys Ala Ala Glu Ser Arg Pro Ala Pro Phe Leu Ile His
        195                 200                 205

Gln Glu Ser Asn Val Ile Val Arg Ala Phe Arg Asp Tyr Leu Arg Gln
        210                 215                 220

Asp Ile Gly Glu Ile Leu Ile Asp Asn Pro Lys Val Leu Glu Leu Ala
225                 230                 235                 240

Arg Gln His Ile Ala Ala Leu Gly Arg Pro Asp Phe Ser Ser Lys Ile
                245                 250                 255

Lys Leu Tyr Thr Gly Glu Ile Pro Leu Phe Ser His Tyr Gln Ile Glu
                260                 265                 270

Ser Gln Ile Glu Ser Ala Phe Gln Arg Glu Val Arg Leu Pro Ser Gly
        275                 280                 285

Gly Ser Ile Val Ile Asp Ser Thr Glu Ala Leu Thr Ala Ile Asp Ile
        290                 295                 300

Asn Ser Ala Arg Ala Thr Arg Gly Gly Asp Ile Glu Glu Thr Ala Phe
305                 310                 315                 320

Asn Thr Asn Leu Glu Ala Ala Asp Glu Ile Ala Arg Gln Leu Arg Leu
                325                 330                 335

Arg Asp Leu Gly Gly Leu Ile Val Ile Asp Phe Ile Asp Met Thr Pro
                340                 345                 350

Val Arg His Gln Arg Ala Val Glu Asn Arg Leu Arg Glu Ala Val Arg
        355                 360                 365

Gln Asp Arg Ala Arg Ile Gln Ile Ser His Ile Ser Arg Phe Gly Leu
        370                 375                 380

Leu Glu Met Ser Arg Gln Arg Leu Ser Pro Ser Leu Gly Glu Ser Ser
385                 390                 395                 400

His His Val Cys Pro Arg Cys Ser Gly Thr Gly Thr Val Arg Asp Asn
                405                 410                 415

Glu Ser Leu Ser Leu Ser Ile Leu Arg Leu Ile Glu Glu Ala Leu
                420                 425                 430

Lys Glu Asn Thr Gln Glu Val His Ala Ile Val Pro Val Pro Ile Ala
        435                 440                 445

Ser Tyr Leu Leu Asn Glu Lys Arg Ser Ala Val
        450                 455

<210> SEQ ID NO 2
<211> LENGTH: 426
<212> TYPE: PRT
<213> ORGANISM: Escherichia coli

<400> SEQUENCE: 2

Met Lys Arg Met Leu Ile Asn Ala Thr Gln Gln Glu Glu Leu Arg Val
1               5                   10                  15

Ala Leu Val Asp Gly Gln Arg Leu Tyr Asp Leu Asp Ile Glu Ser Pro
                20                  25                  30

Gly His Glu Gln Lys Lys Ala Asn Ile Tyr Lys Gly Lys Ile Thr Arg
        35                  40                  45

Ile Glu Pro Ser Leu Glu Ala Ala Phe Val Asp Tyr Gly Ala Glu Arg
        50                  55                  60

His Gly Phe Leu Pro Leu Lys Glu Ile Ala Arg Glu Tyr Phe Pro Ala
65                  70                  75                  80

Asn Tyr Ser Ala His Gly Arg Pro Asn Ile Lys Asp Val Leu Arg Glu
                85                  90                  95

Gly Gln Glu Val Ile Val Gln Ile Asp Lys Glu Glu Arg Gly Asn Lys
                100                 105                 110
```

Gly Ala Ala Leu Thr Thr Phe Ile Ser Leu Ala Gly Ser Tyr Leu Val
                115                 120                 125

Leu Met Pro Asn Asn Pro Arg Ala Gly Gly Ile Ser Arg Arg Ile Glu
            130                 135                 140

Gly Asp Asp Arg Thr Glu Leu Lys Glu Ala Leu Ala Ser Leu Glu Leu
145                 150                 155                 160

Pro Glu Gly Met Gly Leu Ile Val Arg Thr Ala Gly Val Gly Lys Ser
                165                 170                 175

Ala Glu Ala Leu Gln Trp Asp Leu Ser Phe Arg Leu Lys His Trp Glu
            180                 185                 190

Ala Ile Lys Lys Ala Ala Glu Ser Arg Pro Ala Pro Phe Leu Ile His
            195                 200                 205

Gln Glu Ser Asn Val Ile Val Arg Ala Phe Arg Asp Tyr Leu Arg Gln
            210                 215                 220

Asp Ile Gly Glu Ile Leu Ile Asp Asn Pro Lys Val Leu Glu Leu Ala
225                 230                 235                 240

Arg Gln His Ile Ala Ala Leu Gly Arg Pro Asp Phe Ser Ser Lys Ile
                245                 250                 255

Lys Leu Tyr Thr Gly Glu Ile Pro Leu Phe Ser His Tyr Gln Ile Glu
            260                 265                 270

Ser Gln Ile Glu Ser Ala Phe Gln Arg Glu Val Arg Leu Pro Ser Gly
            275                 280                 285

Gly Ser Ile Val Ile Asp Ser Thr Glu Ala Leu Thr Ala Ile Asp Ile
            290                 295                 300

Asn Ser Ala Arg Ala Thr Arg Gly Gly Asp Ile Glu Glu Thr Ala Phe
305                 310                 315                 320

Asn Thr Asn Leu Glu Ala Ala Asp Glu Ile Ala Arg Gln Leu Arg Leu
                325                 330                 335

Arg Asp Leu Gly Gly Leu Ile Val Ile Asp Phe Ile Asp Met Thr Pro
            340                 345                 350

Val Arg His Gln Arg Ala Val Glu Asn Arg Leu Arg Glu Ala Val Arg
            355                 360                 365

Gln Asp Arg Ala Arg Ile Gln Ile Ser His Ile Ser Arg Phe Gly Leu
            370                 375                 380

Leu Glu Met Ser Arg Gln Arg Leu Ser Pro Ser Leu Gly Glu Ser Ser
385                 390                 395                 400

His His Val Cys Pro Arg Cys Ser Gly Thr Gly Thr Val Arg Asp Asn
                405                 410                 415

Glu Ser Leu Ser Cys Ala Gln Ile Gly Cys
            420                 425

<210> SEQ ID NO 3
<211> LENGTH: 1061
<212> TYPE: PRT
<213> ORGANISM: Escherichia coli

<400> SEQUENCE: 3

Met Lys Arg Met Leu Ile Asn Ala Thr Gln Gln Glu Glu Leu Arg Val
1               5                   10                  15

Ala Leu Val Asp Gly Gln Arg Leu Tyr Asp Leu Asp Ile Glu Ser Pro
            20                  25                  30

Gly His Glu Gln Lys Lys Ala Asn Ile Tyr Lys Gly Lys Ile Thr Arg
        35                  40                  45

-continued

```
Ile Glu Pro Ser Leu Glu Ala Ala Phe Val Asp Tyr Gly Ala Glu Arg
 50                  55                  60

His Gly Phe Leu Pro Leu Lys Glu Ile Ala Arg Glu Tyr Phe Pro Ala
 65                  70                  75                  80

Asn Tyr Ser Ala His Gly Arg Pro Asn Ile Lys Asp Val Leu Arg Glu
                 85                  90                  95

Gly Gln Glu Val Ile Val Gln Ile Asp Lys Glu Arg Gly Asn Lys
            100                 105                 110

Gly Ala Ala Leu Thr Thr Phe Ile Ser Leu Ala Gly Ser Tyr Leu Val
            115                 120                 125

Leu Met Pro Asn Asn Pro Arg Ala Gly Gly Ile Ser Arg Ile Glu
130                 135                 140

Gly Asp Asp Arg Thr Glu Leu Lys Glu Ala Leu Ala Ser Leu Glu Leu
145                 150                 155                 160

Pro Glu Gly Met Gly Leu Ile Val Arg Thr Ala Gly Val Gly Lys Ser
                165                 170                 175

Ala Glu Ala Leu Gln Trp Asp Leu Ser Phe Arg Leu Lys His Trp Glu
            180                 185                 190

Ala Ile Lys Lys Ala Ala Glu Ser Arg Pro Ala Pro Phe Leu Ile His
            195                 200                 205

Gln Glu Ser Asn Val Ile Val Arg Ala Phe Arg Asp Tyr Leu Arg Gln
210                 215                 220

Asp Ile Gly Glu Ile Leu Ile Asp Asn Pro Lys Val Leu Glu Leu Ala
225                 230                 235                 240

Arg Gln His Ile Ala Ala Leu Gly Arg Pro Asp Phe Ser Ser Lys Ile
                245                 250                 255

Lys Leu Tyr Thr Gly Glu Ile Pro Leu Phe Ser His Tyr Gln Ile Glu
            260                 265                 270

Ser Gln Ile Glu Ser Ala Phe Gln Arg Glu Val Arg Leu Pro Ser Gly
            275                 280                 285

Gly Ser Ile Val Ile Asp Ser Thr Glu Ala Leu Thr Ala Ile Asp Ile
290                 295                 300

Asn Ser Ala Arg Ala Thr Arg Gly Gly Asp Ile Glu Glu Thr Ala Phe
305                 310                 315                 320

Asn Thr Asn Leu Glu Ala Ala Asp Glu Ile Ala Arg Gln Leu Arg Leu
                325                 330                 335

Arg Asp Leu Gly Gly Leu Ile Val Ile Asp Phe Ile Asp Met Thr Pro
            340                 345                 350

Val Arg His Gln Arg Ala Val Glu Asn Arg Leu Arg Glu Ala Val Arg
            355                 360                 365

Gln Asp Arg Ala Arg Ile Gln Ile Ser His Ile Ser Arg Phe Gly Leu
370                 375                 380

Leu Glu Met Ser Arg Gln Arg Leu Ser Pro Ser Leu Gly Glu Ser Ser
385                 390                 395                 400

His His Val Cys Pro Arg Cys Ser Gly Thr Gly Thr Val Arg Asp Asn
                405                 410                 415

Glu Ser Leu Ser Leu Ser Ile Leu Arg Leu Ile Glu Glu Ala Leu
            420                 425                 430

Lys Glu Asn Thr Gln Glu Val His Ala Ile Val Pro Val Pro Ile Ala
            435                 440                 445

Ser Tyr Leu Leu Asn Glu Lys Arg Ser Ala Val Asn Ala Ile Glu Thr
450                 455                 460
```

-continued

```
Arg Gln Asp Gly Val Arg Cys Val Ile Val Pro Asn Asp Gln Met Glu
465                 470                 475                 480

Thr Pro His Tyr His Val Leu Arg Val Arg Lys Gly Glu Glu Thr Pro
            485                 490                 495

Thr Leu Ser Tyr Met Leu Pro Lys Leu His Glu Glu Ala Met Ala Leu
            500                 505                 510

Pro Ser Glu Glu Glu Phe Ala Glu Arg Lys Arg Pro Glu Gln Pro Ala
            515                 520                 525

Leu Ala Thr Phe Ala Met Pro Asp Val Pro Ala Pro Thr Pro Ala
        530                 535                 540

Glu Pro Ala Ala Pro Val Val Ala Pro Ala Pro Lys Ala Pro Ala
545                 550                 555                 560

Thr Pro Ala Thr Pro Ala Gln Pro Gly Leu Leu Ser Arg Phe Phe Gly
            565                 570                 575

Ala Leu Lys Ala Leu Phe Ser Gly Gly Glu Glu Thr Lys Pro Thr Glu
            580                 585                 590

Gln Pro Ala Pro Lys Ala Glu Ala Lys Pro Glu Arg Gln Gln Asp Arg
            595                 600                 605

Arg Lys Pro Arg Gln Asn Asn Arg Arg Asp Arg Asn Glu Arg Arg Asp
    610                 615                 620

Thr Arg Ser Glu Arg Thr Glu Gly Ser Asp Asn Arg Glu Glu Asn Arg
625                 630                 635                 640

Arg Asn Arg Arg Gln Ala Gln Gln Thr Ala Glu Thr Arg Glu Gly
            645                 650                 655

Arg Gln Gln Ala Glu Val Thr Glu Lys Ala Arg Thr Ala Asp Glu Gln
            660                 665                 670

Gln Ala Pro Arg Arg Glu Arg Ser Arg Arg Asn Asp Asp Lys Arg
            675                 680                 685

Gln Ala Gln Gln Glu Ala Lys Ala Leu Asn Val Glu Glu Gln Ser Val
    690                 695                 700

Gln Glu Thr Glu Gln Glu Glu Arg Val Arg Pro Val Gln Pro Arg Arg
705                 710                 715                 720

Lys Gln Arg Gln Leu Asn Gln Lys Val Arg Tyr Glu Gln Ser Val Ala
            725                 730                 735

Glu Glu Thr Val Val Ala Pro Val Ala Glu Glu Thr Val Ala Ala Glu
            740                 745                 750

Pro Ile Val Gln Glu Ala Pro Ala Pro Arg Thr Glu Leu Val Lys Val
            755                 760                 765

Pro Leu Pro Val Val Ala Gln Thr Ala Pro Glu Gln Gln Glu Glu Asn
            770                 775                 780

Asn Ala Asp Asn Arg Asp Asn Gly Gly Met Pro Arg Arg Ser Arg Arg
785                 790                 795                 800

Ser Pro Arg His Leu Arg Val Ser Gly Gln Arg Arg Arg Tyr Arg
            805                 810                 815

Asp Glu Arg Tyr Pro Thr Gln Ser Pro Met Pro Leu Thr Val Ala Cys
            820                 825                 830

Ala Ser Pro Glu Leu Ala Ser Gly Lys Val Trp Ile Arg Tyr Pro Ile
            835                 840                 845

Val Arg Pro Gln Asp Val Gln Val Glu Glu Arg Glu Gln Glu Glu
    850                 855                 860

Val Gln Val Gln Pro Met Val Thr Glu Val Pro Val Ala Ala Ala Val
865                 870                 875                 880

Glu Pro Val Val Ser Ala Pro Val Val Glu Glu Met Ala Glu Val Val
```

-continued

```
                          885                 890                 895
Glu Ala Pro Val Pro Val Ala Glu Pro Gln Pro Glu Val Val Glu Thr
            900                 905                 910
Thr His Pro Glu Val Ile Ala Ala Val Thr Glu Gln Pro Gln Val
            915                 920                 925
Ile Thr Glu Ser Asp Val Ala Val Ala Gln Glu Val Ala Glu His Ala
    930                 935                 940
Glu Pro Val Val Glu Pro Gln Glu Thr Ala Asp Ile Glu Glu Val
945                 950                 955                 960
Ala Glu Thr Ala Glu Val Val Val Ala Glu Pro Glu Val Val Ala Gln
            965                 970                 975
Pro Ala Ala Pro Val Val Ala Glu Val Ala Ala Glu Val Glu Thr Val
            980                 985                 990
Thr Ala Val Lys Pro Glu Ile Thr  Val Glu His Asn His  Ala Thr Ala
            995                1000                1005
Pro Met  Thr Arg Ala Pro Ala  Pro Glu Tyr Val Pro  Glu Ala Pro
    1010                1015                1020
Arg His  Ser Asp Trp Gln Arg  Pro Thr Phe Ala Phe  Glu Gly Lys
    1025                1030                1035
Gly Ala  Ala Gly Gly His Thr  Ala Thr His His Ala  Ser Ala Ala
    1040                1045                1050
Pro Ala  Arg Pro Gln Pro Val  Glu
    1055                1060
```

<210> SEQ ID NO 4
<211> LENGTH: 5475
<212> TYPE: DNA
<213> ORGANISM: Escherichia coli
<220> FEATURE:
<221> NAME/KEY: Intron
<222> LOCATION: (1260)..(4636)
<220> FEATURE:
<221> NAME/KEY: Intron
<222> LOCATION: (1260)..(4636)

<400> SEQUENCE: 4

```
atgaaaagaa tgttaatcaa cgcaactcag caggaagagt tgcgcgttgc ccttgtagat    60
gggcagcgtc tgtatgacct ggatatcgaa agtccagggc acgagcagaa aaaggcaaac   120
atctacaaag gtaaaatcac ccgcattgaa ccgagtctgg aagctgcttt tgttgattac   180
ggcgctgaac gtcacggttt cctcccacta aaagaaattg cccgcgaata tttccctgct   240
aactacagtg ctcatggtcg tcccaacatt aaagatgtgt tgcgtgaagg tcaggaagtc   300
attgttcaga tcgataaaga agagcgcggc aacaaaggcg cggcattaac caccttatc   360
agtctggcgg gtagctatct ggttctgatg ccgaacaacc cgcgcgcggg tggcatttct   420
cgccgtatcg aaggcgacga ccgtaccgaa ttaaaagaag cactggcaag ccttgaactg   480
ccggaaggca tgggcttat cgtgcgcacc gctggcgtcg gcaaatctgc tgaggcgctg   540
caatgggatt taagcttccg tctgaaacac tgggaagcca tcaaaaaagc cgctgaaagc   600
cgcccggccc cgttcctgat tcatcaggag agcaacgtaa tcgttcgcgc attccgcgat   660
tacttacgtc aggacatcgg cgaaatcctt atcgataacc cgaaagtgct cgaactggca   720
cgtcagcata tcgctgcatt aggtcgcccg gatttcagca gcaaaatcaa actgtacacc   780
ggcgagatcc cgctgttcag ccactaccag atcgagtcac agatcgagtc cgccttccag   840
cgtgaagttc gtctgccgtc tggtggttcc attgttatcg acagcaccga agcgttaacg    900
```

```
gccatcgaca tcaactccgc acgcgcgacc cgcggcggcg atatcgaaga aaccgcgttt      960
aacactaacc tcgaagctgc cgatgagatt gctcgtcagc tgcgcctgcg tgacctcggc     1020
ggcctgattg ttatcgactt catcgacatg acgccagtac gccaccagcg tgcggtagaa     1080
aaccgtctgc gtgaagcggt gcgtcaggac cgtgcgcgta ttcaaatcag ccatatttct     1140
cgctttggcc tgctggaaat gtcccgtcag cgcctgagcc catcactggg tgaatccagt     1200
catcacgttt gtccgcgttg ttctggtact ggcaccgtgc gtgacaacga atcgctgtcg     1260
tgcgcccaga tagggtgtta agtcaagtag tttaaggtac tactctgtaa gataacacag     1320
aaaacagcca acctaaccga aaagcgaaag ctgatacggg aacagagcac ggttggaaag     1380
cgatgagtta cctaaagaca atcgggtacg actgagtcgc aatgttaatc agatataagg     1440
tataagttgt gtttactgaa cgcaagtttc taatttcggt ttcacgtcga tagaggaaag     1500
tgtctgaaac ctctagtaca aagaaaggta agttacgtta accgacttat ctgttatcac     1560
cacatttgta caatctgtag gagaacctat gggaacgaaa cgaaagcgat gccgagaatc     1620
tgaatttacc aagacttaac actaactggg gatacccctaa caagaatgc ctaatagaaa     1680 ggaggaaaaa ggctatagca ctagagcttg aaaatcttgc aagggtacgg agtactcgta     1740
gtagtctgag aagggtaacg ccctttacat ggcaaagggg tacagttatt gtgtactaaa     1800
attaaaaatt gattagggag gaaaacctca aaatgaaacc aacaatggca atttttagaaa     1860 gaatcagtaa aaattcacaa gaaaatatag acgaagtttt tacaagactt tatcgttatc     1920
ttttacgtcc agatatttat tacgtggcga cgcgtactaa aacaattcat ccagtaaaat     1980
ataatatttt attttctccc aatcaggctt gatccccagt aagtcaaaaa atagctcgac     2040
atactgttct tccccgatat cctccctgat cgaccggacg cagaaggcaa tgtcatacca     2100
cttgtccgcc ctgccgcttc tcccaagatc aataaagcca cttactttgc catctttcac     2160
aaagatgttg ctgtctccca ggtcgccgtg ggaaaagaca agttcctctt cgggcttttc     2220
cgtctttaaa aaatcataca gctctcttgg gttaattgag gcctgagtat aaggtgactt     2280
atacttgtaa tctatctaaa cggggaacct ctctagtaga caatcccgtg ctaaattgta     2340
ggactgccct ttaataaata cttctatatt taaagaggta tttatgaaaa gcggaattta     2400
tcagattaaa aatactttct ctagagaaaa tttcgtctgg attagttact tatcgtgtaa     2460
aatctgataa atggaattgg ttctacataa atgcctaacg actatcccctt tggggagtag     2520 ggtcaagtga ctcgaaacga tagacaactt gctttaacaa gttggagata tagtctgctc     2580
tgcatggtga catgcagctg gatataattc cggggtaaga ttaacgacct tatctgaaca     2640
taatgcttta aatggagtgt cttcttccca gttttcgcaa tccacatcgg ccagatcgtt     2700
attcagtaag taatccaatt cggctaagcg gctgtctaag ctattcgtat agggacaatc     2760
cgatatgtcg atggagtgaa agagcctgat gcactccgca tacagctcga taatctttc      2820 agggctttgt tcatcttcat actcttccga gcaaggacg ccatcggcct cactcatgag      2880
cagattgctc cagccatcat gccgttcaaa gtgcaggacc tttggaacag gcagctttcc     2940
ttccagccat agcatcatgt cctttttccg ttccacatca taggtggtcc ctttataccg     3000
gctgtccgtc attttttaaat ataggttttc attttctccc accagcttat ataccttagc    3060
aggagacatt ccttccgtat cttttacgca gcggtatttt tcgatcagtt ttttcaattc     3120
cggtgatatt ctcattttag ccatttatta tttccttcct cttttctaca gtatttaaag     3180
ataccccaag aagctaatta taacaagacg aactccaatt cactgttcct tgcattctaa     3240
aaccttaaat accagaaaac agcttttttca aagttgtttt caagttggc gtataacata      3300
```

-continued

```
gtatcgacgg agccgatttt gaaacgcgtt gggaaatggc aatgatagcg aaacaacgta    3360
aaactcttgt tgtatgcttt cattgtcatc gtcacgtgat tcataaacac aagtgaatgt    3420
cgacagtgaa tttttacgaa cgaacaataa cagagccgta tactccgaga ggggtacgta    3480
cggttcccga agagggtggt gcaaaccagt cacagtaatg tgaacaaggc ggtacctccc    3540
tacttcacgc tctctattct gcgtctgatc gaagaagaag cgctgaaaga aacacccag     3600 gaagttcacg ccattgttcc tgtgccaatc gcttcttacc tgctgaatga aaaacgttct    3660
gcggtaaatg ccattgaaac tcgtcaggac ggtgtgcgct gtgtaattgt gccaaacgat    3720
cagatggaaa ccccgcacta ccacgtgctg cgcgtgcgta aggggaagaa accccaacc     3780 ttaagctaca tgctgccgaa gctgcatgaa gaagcgatgg cgctgccgtc tgaagaagag    3840
ttcgctgaac gtaagcgtcc ggaacaacct gcgctggcaa cctttgccat gccggatgtg    3900
ccgcctgcgc caacgccagc tgaacctgcc gcgcctgttg tagctccagc accgaaagct    3960
gcaccggcaa caccagcagc tcctgcacaa cctgggctgt gagccgctt  cttcggcgca    4020 ctgaaagcgc tgttcagcgg tggtgaagaa accaaaccga ccgagcaacc agcaccgaaa    4080
gcagaagcga accggaacg  tcaacaggat cgtcgcaagc ctcgtcagaa caaccgccgt    4140
gaccgtaatg agcgccgcga cacccgtagt gaacgtactg aaggcagcga taatcgcgaa    4200
gaaaaccgtc gtaatcgtcg ccaggcacag cagcagactc cgagacgcg  tgagagccgt    4260 cagcaggctg aggtaacgga aaaagcgcgt accgccgacg agcagcaagc gccgcgtcgt    4320
gaacgtagcc gccgccgtaa tgatgataaa cgtcaggcgc aacaagaagc gaaggcgctg    4380
aatgttgaag agcaatctgt tcaggaaacc gaacaggaag aacgtgtacg tccggttcag    4440
ccgcgtcgta acagcgtca  gctcaatcag aaagtgcgtt acgagcaaag cgtagccgaa    4500
gaagcggtag tcgcaccggt ggttgaagaa actgtcgctg ccgaaccaat tgttcaggaa    4560
gcgccagctc cacgcacaga actggtgaaa gtcccgctgc cagtcgtagc gcaaactgca    4620
ccagaacagc aagaagagaa caatgctgat aaccgtgaca acggtggcat gccgcgtcgt    4680
tctcgccgct cgcctcgtca cctgcgcgta agtggtcagc gtcgtcgtcg ctatcgtgac    4740
gagcgttatc caacccagtc gccaatgccg ttgaccgtag cgtgcgcgtc tccggaactg    4800
gcctctggca aagtctggat ccgctatcca attgtacgtc cgcaagatgt acaggttgaa    4860
gagcagcgcg aacaggaaga agtacatgtg cagccgatgg tgactgaggt ccctgtcgcc    4920
gccgctatcg aaccggttgt tagcgcgcca gttgttgaag aagtggccgg tgtcgtagaa    4980
gcccccgttc aggttgccga accgcaaccg gaagtggttg aaacgacgca tcctgaagtg    5040
atcgctgccg cggtaactga acagccgcag gtgattaccg agtctgatgt tgccgtagcc    5100
caggaagttg cagaacaagc agaaccggtg gttgaaccgc aggaagagac ggcagatatt    5160
gaagaagttg tcgaaactgc tgaggttgta gttgctgaac ctgaagttgt tgctcaacct    5220
gccgcgccag tagtcgctga agtcgcagca gaagttgaaa cggtagctgc ggtcgaacct    5280
gaggtcaccg ttgagcataa ccacgctacc gcgccaatga cgcgcgctcc agcaccggaa    5340
tatgttccgg aggcaccgcg tcacagtgac tggcagcgcc ctactttgc  cttcgaaggt    5400 aaaggtgccg caggtggtca tacggcaaca catcatgcct ctgccgctcc tgcgcgtccg    5460
caacctgttg agtaa                                                     5475
```

<210> SEQ ID NO 5
<211> LENGTH: 53
<212> TYPE: DNA

-continued

<213> ORGANISM: Escherichia coli

<400> SEQUENCE: 5
aaaaaagctt ataattatcc ttacgaatcg ctgtcgtgcg cccagatagg gtg    53

<210> SEQ ID NO 6
<211> LENGTH: 60
<212> TYPE: DNA
<213> ORGANISM: Escherichia coli

<400> SEQUENCE: 6
cagattgtac aaatgtggtg ataacagata agtcgctgtc gctaacttac ctttctttgt    60

<210> SEQ ID NO 7
<211> LENGTH: 49
<212> TYPE: DNA
<213> ORGANISM: Escherichia coli

<400> SEQUENCE: 7
tgaacgcaag tttctaattt cggttattcg tcgatagagg aaagtgtct    49

<210> SEQ ID NO 8
<211> LENGTH: 1281
<212> TYPE: DNA
<213> ORGANISM: Escherichia coli
<220> FEATURE:
<221> NAME/KEY: Intron
<222> LOCATION: (1260)..(1281)
<220> FEATURE:
<221> NAME/KEY: Intron
<222> LOCATION: (1260)..(1281)

<400> SEQUENCE: 8

| atgaaaagaa tgttaatcaa cgcaactcag caggaagagt tgcgcgttgc ccttgtagat | 60 |
|---|---|
| gggcagcgtc tgtatgacct ggatatcgaa agtccagggc acgagcagaa aaaggcaaac | 120 |
| atctacaaag gtaaaatcac ccgcattgaa ccgagtctgg aagctgcttt tgttgattac | 180 |
| ggcgctgaac gtcacggttt cctcccacta aaagaaattg cccgcgaata tttccctgct | 240 |
| aactacagtg ctcatggtcg tcccaacatt aaagatgtgt tgcgtgaagg tcaggaagtc | 300 |
| attgttcaga tcgataaaga agagcgcggc aacaaaggcg cggcattaac cacctttatc | 360 |
| agtctggcgg gtagctatct ggttctgatg ccgaacaacc cgcgcgcggg tggcatttct | 420 |
| cgccgtatcg aaggcgacga ccgtaccgaa ttaaaagaag cactggcaag ccttgaactg | 480 |
| ccggaaggca tggggcttat cgtgcgcacc gctggcgtcg gcaaatctgc tgaggcgctg | 540 |
| caatgggatt taagcttccg tctgaaacac tgggaagcca tcaaaaaagc cgctgaaagc | 600 |
| cgcccggccc cgttcctgat tcatcaggag agcaacgtaa tcgttcgcgc attccgcgat | 660 |
| tacttacgtc aggacatcgg cgaaatcctt atcgataacc cgaaagtgct cgaactggca | 720 |
| cgtcagcata tcgctgcatt aggtcgcccg gatttcagca gcaaaatcaa actgtacacc | 780 |
| ggcgagatcc cgctgttcag ccactaccag atcgagtcac agatcgagtc cgccttccag | 840 |
| cgtgaagttc gtctgccgtc tggtggttcc attgttatcg acagcaccga agcgttaacg | 900 |
| gccatcgaca tcaactccgc acgcgcgacc cgcggcggcg atatcgaaga accgcgttt | 960 |
| aacactaacc tcgaagctgc cgatgagatt gctcgtcagc tgcgcctgcg tgacctcggc | 1020 |
| ggcctgattg ttatcgactt catcgacatg acgccagtac gccaccagcg tgcggtagaa | 1080 |
| aaccgtctgc gtgaagcggt gcgtcaggac cgtgcgcgta ttcaaatcag ccatatttct | 1140 |
| cgctttggcc tgctggaaat gtcccgtcag cgcctgagcc catcactggg tgaatccagt | 1200 |

```
catcacgttt gtccgcgttg ttctggtact ggcaccgtgc gtgacaacga atcgctgtcg    1260
tgcgcccaga tagggtgtta a                                              1281
```